(12) United States Patent
Zettl et al.

(10) Patent No.: US 10,294,524 B2
(45) Date of Patent: May 21, 2019

(54) METHODS OF GENERATION OF PORES IN SHEETS OF HEXAGONAL BORON NITRIDE AND APPLICATIONS THEREOF

(71) Applicants: Alexander K. Zettl, Kensington, CA (US); Gabriel P. Dunn, Berkeley, CA (US); Stephen M. Gilbert, Albany, CA (US)

(72) Inventors: Alexander K. Zettl, Kensington, CA (US); Gabriel P. Dunn, Berkeley, CA (US); Stephen M. Gilbert, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 481 days.

(21) Appl. No.: 15/088,549

(22) Filed: Apr. 1, 2016

(65) Prior Publication Data

US 2016/0334366 A1 Nov. 17, 2016

Related U.S. Application Data

(60) Provisional application No. 62/141,489, filed on Apr. 1, 2015.

(51) Int. Cl.
*C12Q 1/6869* (2018.01)
*G01N 33/487* (2006.01)

(52) U.S. Cl.
CPC ..... *C12Q 1/6869* (2013.01); *G01N 33/48721* (2013.01)

(58) Field of Classification Search
CPC ................. C12Q 1/6869; G01N 33/48721
See application file for complete search history.

(56) References Cited

U.S. PATENT DOCUMENTS

| 8,501,024 B2 | 8/2013 | Zettl |
| 9,611,140 B2 | 4/2017 | Russo |
| 2017/0158487 A1 | 6/2017 | Russo |

OTHER PUBLICATIONS

Y. Lin, et al. "Defect Functionaliztion of Hexagonal Boron Nitride Nanosheets" Journal of Physical Chemistry C, 114(41): p. 17434-17439, Sep. 2010.*
Pacilé, D.; Meyer, J. C.; Girit, C. O.; Zettl, A. The Two-Dimensional Phase of Boron Nitride: Few-Atomic-Layer Sheets and Suspended Membranes. Appl. Phys. Lett. 2008, 92, 133107.
Alem, N.; Erni, R.; Kisielowski, C.; Rossell, M. D.; Gannett, W.; Zettl, A. Atomically Thin Hexagonal Boron Nitride Probed by Ultrahigh-Resolution Transmission Electron Microscopy. Phys. Rev. B 2009, 80, 155425.
Goldberg, D.; Bando, Y.; Huang, Y.; Terao, T.; Mitome, M.; Tang, C.; Zhi, C. Boron Nitride Nanotubes and Nanosheets. ACS Nano 2010, 4, 2979-2993.

(Continued)

*Primary Examiner* — J. Christopher Ball

(57) ABSTRACT

This disclosure provides systems, methods, and apparatus related to few-layer and monolayer hexagonal boron nitride having a pore therein. In one aspect, a method comprises providing a sheet of hexagonal boron nitride (h-BN). A defect is created in the sheet of h-BN. The sheet of h-BN is heated to a temperature above about 500° C. The defect in the sheet of h-BN is irradiated with charged particles to enlarge the defect to a hexagonal-shaped pore or a parallelogram-shaped pore in the sheet of h-BN.

20 Claims, 13 Drawing Sheets

(56) References Cited

OTHER PUBLICATIONS

Meyer, J. C.; Chuvilin, A.; Algara-Siller, G.; Biskupek, J.; Kaiser, U. Selective Sputtering and Atomic Resolution Imaging of Atomically Thin Boron Nitride Membranes. Nano Lett. 2009, 9, 2683-2689.

Alem, N.; Erni, R.; Kisielowski, C.; Rossell, M. D.; Hartel, P.; Jiang, B.; Gannett, W.; Zettl, A. Vacancy Growth and Migration Dynamics in Atomically Thin Hexagonal Boron Nitride under Electron Beam Irradiation. Phys. status solidi-Rapid Res. Lett. 2011, 5, 295-297.

Gibb, A. L.; Alem, N.; Chen, J.-H.; Erickson, K. J.; Ciston, J.; Gautam, A.; Linck, M.; Zettl, A. Atomic Resolution Imaging of Grain Boundary Defects in Monolayer Chemical Vapor Deposition-Grown Hexagonal Boron Nitride. J. Am. Chem. Soc. 2013, 135, 6758-6761.

Lin, Y.; Connell, J. W. Advances in 2D Boron Nitride Nanostructures: Nanosheets, Nanoribbons, Nanomeshes, and Hybrids with Graphene. Nanoscale 2012, 4, 6908-6939.

Jin, C.; Lin, F.; Suenaga, K.; Iijima, S. Fabrication of a Freestanding Boron Nitride Single Layer and Its Defect Assignments. Phys. Rev. Lett. 2009, 102, 195505.

Warner, J. H.; Rümmeli, M. H.; Bachmatiuk, A.; Büchner, B. Atomic Resolution Imaging and Topography of Boron Nitride Sheets Produced by Chemical Exfoliation. ACS Nano 2010, 4, 1299-1304.

Ryu, G. H.; Park, H. J.; Ryou, J.; Park, J.; Lee, J.; Kim, G.; Shin, H. S.; Bielawski, C. W.; Ruoff, R. S.; Hong, S.; et al. Atomic-Scale Dynamics of Triangular Hole Growth in Monolayer Hexagonal Boron Nitride under Electron Irradiation. Nanoscale 2015, 7, 10600-10605.

Cretu, O.; Lin, Y.-C.; Suenaga, K. Inelastic Electron Irradiation Damage in Hexagonal Boron Nitride. Micron 2015, 72, 21-27.

Cretu, O.; Lin, Y.-C.; Koshino, M.; Tizei, L. H. G.; Liu, Z.; Suenaga, K. Structure and Local Chemical Properties of Boron-Terminated Tetravacancies in Hexagonal Boron Nitride. Phys. Rev. Lett. 2015, 114, 075502.

Zhou, Z.; Hu, Y.; Wang, H.; Xu, Z.; Wang, W.; Bai, X.; Shan, X.; Lu, X. DNA Translocation through Hydrophilic Nanopore in Hexagonal Boron Nitride. Sci. Rep. 2013, 3, 3287.

Liu, S.; Lu, B.; Zhao, Q.; Li, J.; Gao, T.; Chen, Y.; Zhang, Y.; Liu, Z.; Fan, Z.; Yang, F.; et al. Boron Nitride Nanopores: Highly Sensitive DNA Single-Molecule Detectors. Adv. Mater. 2013, 25, 4549-4554.

\* cited by examiner

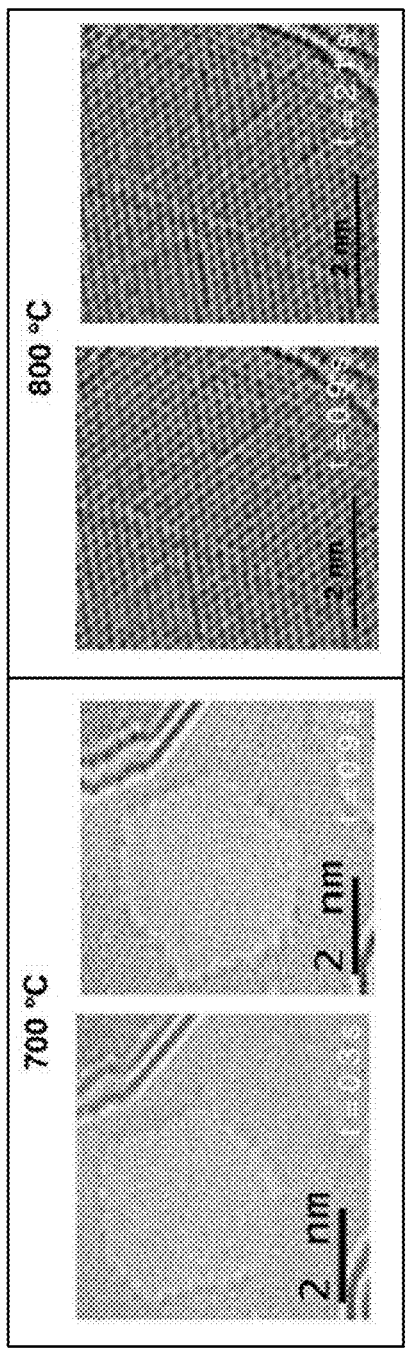
FIG. 4A
FIG. 4B
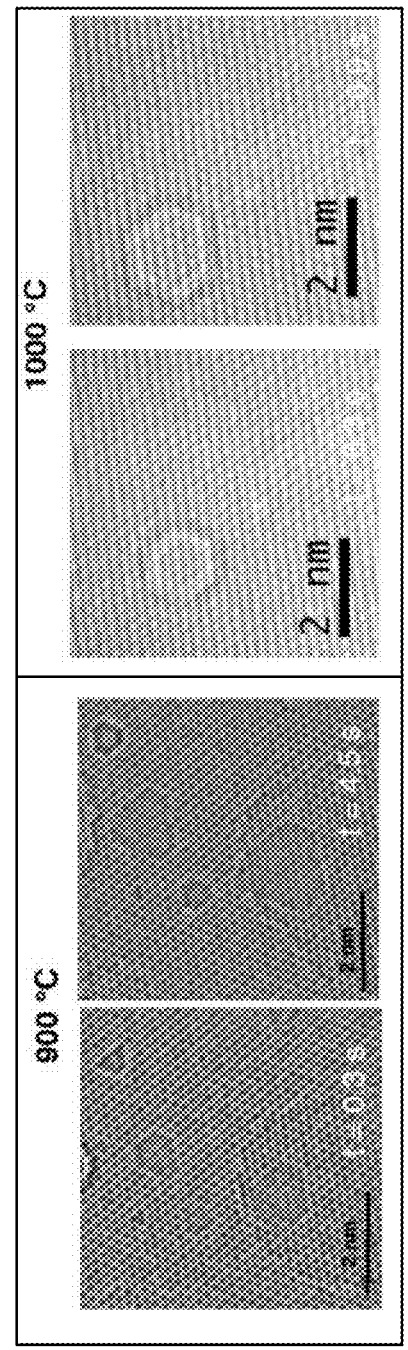
FIG. 4C
FIG. 4D

FIG. 5A
FIG. 5B
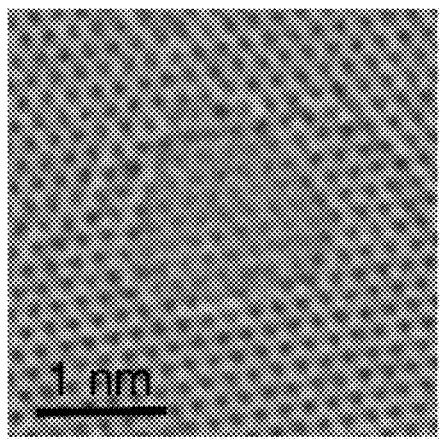
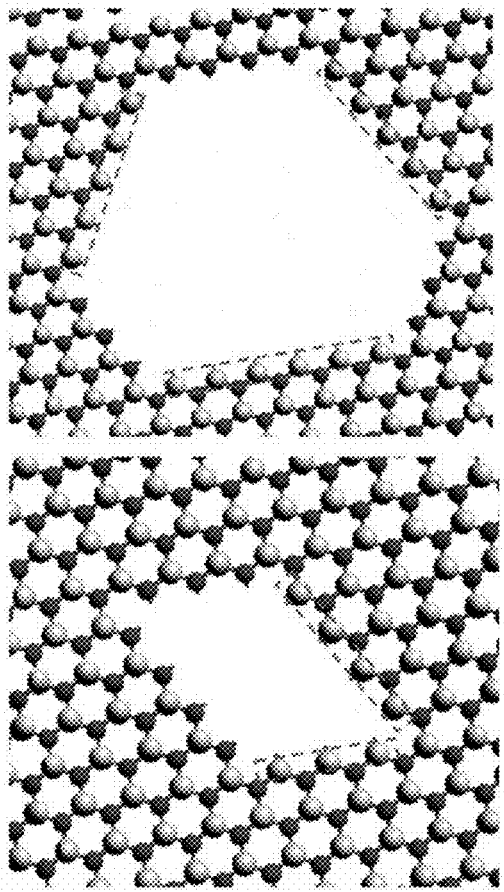
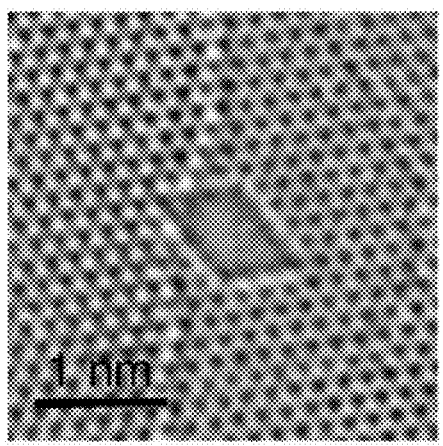
FIG. 5C
FIG. 5D

METHODS OF GENERATION OF PORES IN SHEETS OF HEXAGONAL BORON NITRIDE AND APPLICATIONS THEREOF

STATEMENT OF GOVERNMENT SUPPORT

This invention was made with government support under Contract No. DE-AC02-05CH11231 awarded by the U.S. Department of Energy, under MURI award N00014-09-1-1066 awarded by the Office of Naval Research, under Grant No. FA9950-10-1-0451 awarded by the Air Force Office of Scientific Research, and under Grant No. HDTRA1-15-1-0036 awarded by the Defense Threat Reduction Agency. The government has certain rights in this invention.

RELATED APPLICATIONS

This application is related to U.S. Provisional Patent Application Ser. No. 62/141,489, filed Apr. 1, 2015, which is herein incorporated by reference.

TECHNICAL FIELD

This disclosure relates generally to few-layer and monolayer hexagonal boron nitride and more particularly to few-layer and monolayer hexagonal boron nitride with pores therein.

BACKGROUND

Monolayer graphite (i.e., graphene) has attracted interest over the past decade, which has in turn spurred interest in few-layer and monolayer hexagonal boron nitride (h-BN). Independent of the number of layers, h-BN is a wide band gap (~5.5 eV) insulator with higher oxidation resistance than, and comparable mechanical strength to, graphene. These and other characteristics make h-BN a potential candidate in various applications such as filler for mechanically enhanced polymer composites, oxidation resistant coatings for aerospace technologies, neutron shielding barriers, and scaffolds for high temperature combustion gas sensors. As a substrate for other 2D materials, h-BN has been shown to reduce charge density fluctuation and surface roughness, leading to enhance electronic properties in overlaid graphene and enhanced optoelectronic properties in overlaid transitional metal dichalcogenides.

Despite these novel characteristics and promising applications, the intrinsic properties of few-layer h-BN, in particular structural properties, have not been studied as extensively as those for graphene. Limited electron microscopy investigations of h-BN have revealed the atomic structure of point defects, step edges, and grain boundaries at room temperature, and grain boundaries at 450° C., but analogous high temperature (above 500° C.) defect formation, stability, and dynamics studies are very limited. The elevated temperature atomic-scale characteristics of h-BN are important in understanding the physical, mechanical and chemical properties of h-BN for future harsh-environment applications.

SUMMARY

Described herein are single layer or few-layer hexagonal boron nitride (h-BN) porous sheets or membranes, methods of fabrication for the pores, and applications of the sheets of h-BN in devices and nanodevices. Some advantages of h-BN sheets over graphene sheets include more precisely controlled pore size in h-BN sheets, stable nitrogen endgroups in h-BN, and reduced electrochemical background for DNA sequencing with h-BN.

The pores provided comprise atomic vacancies in h-BN can be up to 50 nanometers (nm) in length. The shape and size of a pore can be precisely controlled. A pore can have the shape of a triangle, a parallelogram, a hexagon, a circle, or an oval. At the edge of a pore, the hexagonal boron nitride can be bare, contain interlayer bonds, or be functionalized to control the motion or storage of chemical species at the pore.

Methods for creating pores of controllable size and shape using single atomic layer thick and multiple atomic layer thick sheets of h-BN have been developed. The methods allow for highly repeatable pore creation with sub-nanometer precision.

For example, the pores can be created using an electron beam of a transmission electron microscope (TEM). It has been shown that an electron beam will preferentially eject individual boron atoms from a sheet of h-BN. After a single boron atom is removed from the material, the neighboring boron atoms become more weakly bound. The hole then widens in a quantized fashion as the electron beam strips away sequential series of neighboring atoms. At room temperature, this electron beam method creates triangular pores of controllable size. By elevating the temperature, the shape of the resulting pores can be controlled, forming parallelograms, hexagons, circles, or ovals. The size of the pore can be continuously monitored in the TEM and the electron beam can be shut off when the pore is a specified size. This allows for the repeatable fabrication of pores of the same size down to the atomic level.

A sheet of h-BN with a single pore can be used to separate two reservoirs containing an ionic solution. By adding an analyte species to one reservoir and applying a voltage between the reservoirs, this configuration can be used to sequence DNA or analyze molecules. For molecular analysis, molecular species can be sorted and classified by size.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIGS. 4A-4D show HRTEM images of hexagonal defects at 700° C., 800° C., 900° C., and 1000° C. The time label in each image indicates when the image was taken in a particular fixed-temperature time-series.

FIGS. 5A-5D show HRTEM images and corresponding atomic models of hexagon and parallelogram-shaped defects (at 900° C.) showing the presence of both N and B-terminated zigzag edges.

DETAILED DESCRIPTION

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Various techniques and mechanisms of the present invention will sometimes be described in singular form for clarity. However, it should be noted that some embodiments include multiple iterations of a technique or multiple instantiations of a mechanism unless noted otherwise.

Figure 1A:
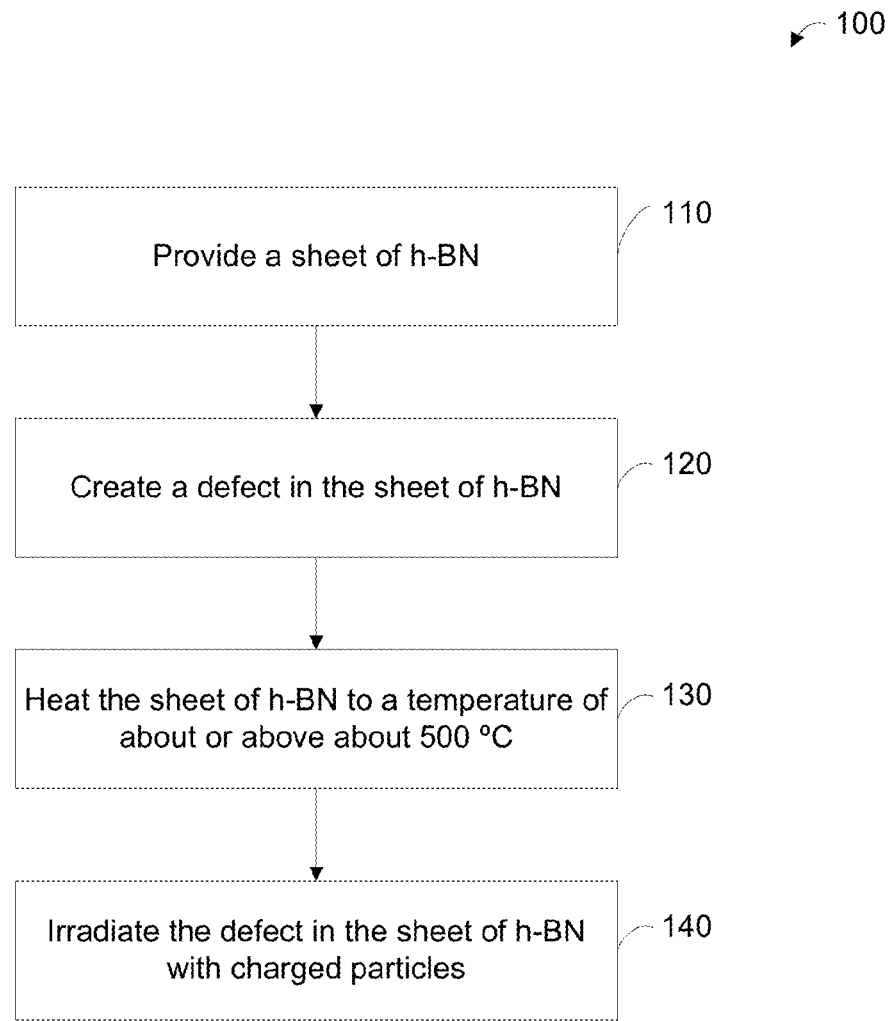
FIG. 1A shows an example of a flow diagram illustrating a method of forming a pore in a sheet of h-BN.

FIG. 1A shows an example of a flow diagram illustrating a method of forming a pore in a sheet of hexagonal boron nitride (h-BN). In some embodiments, the method shown in FIG. 1A is used to form a pore having a specified shape in a sheet of h-BN. A pore may be referred to as a nanopore in the scientific literature. At block 110 of the method 100, a sheet of h-BN is provided. In some embodiments, the sheet of h-BN is a monolayer of h-BN. In some embodiments, the sheet of h-BN comprises multiple layers of monolayer h-BN (e.g., a few-layer sheet of h-BN is provided). In some embodiments, the sheet of h-BN comprises 2 to 6, 2 to 5, 2 to 3, or 2 layers of monolayer h-BN. In some embodiments, the sheet of h-BN has a thickness of about 0.3 nanometers (nm) to 2 nm. The terms "about" or "approximate" and the like are synonymous and are used to indicate that the value modified by the term has an understood range associated with it, where the range can be ±10%, ±5%, or ±1%.

In some embodiments, prior to block 110, the sheet of h-BN is fabricated. For example, a sheet of h-BN may be fabricated by a carbothermic reduction reaction between highly oriented pyrolytic graphite flakes, boron oxide powder, and nitrogen gas. See U.S. Pat. No. 8,501,024, for example, for further details regarding the fabrication of sheets of h-BN.

At block 120, a defect is created in the sheet of h-BN. In some embodiments, the defect is a vacancy (e.g., a missing boron atom or a missing nitrogen atom in a monolayer of h-BN) or a single vacancy. In some embodiments, the defect is 2 to 20 or 2 to 10 vacancies adjacent to one another or proximate to one another in the sheet of h-BN. In some embodiments, the defect is numerous vacancies adjacent to one another or proximate to one another in the sheet of h-BN. For example, numerous vacancies may form a void (i.e., an open area) in a monolayer of h-BN or in few-layer h-BN.

In some embodiments, a defect is created in the sheet of h-BN by irradiating the sheet of h-BN with charged particles. Irradiating a sheet of h-BN with charged particles is described further with respect to block 140. In some embodiments, the charged particles used at block 120 have similar or the same characteristics as the charged particles used at block 140. In some embodiments, the sheet of h-BN is irradiated with charged particles for about 0.5 seconds to 60 seconds to form a defect in the sheet of h-BN.

In some embodiments, a catalyst is deposited on the surface of the sheet of h-BN. The catalyst may then be heated (e.g., with a laser) to form a defect in the sheet of h-BN when the catalyst reacts with the sheet of h-BN. For example, the catalyst may be deposited on the surface of the sheet of h-BN by evaporation, chemical vapor deposition (CVD), atomic layer deposition (ALD), sputtering, or other deposition techniques. In some embodiments, the catalyst is a transition metal. For example, the catalyst may be iron, cobalt, or nickel. In some embodiments, a single atom of the catalyst is deposited on the surface of the sheet of h-BN. In some embodiments, a small cluster of atoms of the catalyst is deposited on the surface of the sheet of h-BN. In some embodiments, the catalyst is a nanoparticle. In some embodiments, the catalyst has dimensions of about 1 nm or less than about 1 nm.

Photolithography techniques may be used to define where the catalyst is deposited on the surface of the sheet of h-BN. For example, in some embodiments, a photoresist is deposited on the surface of the sheet of h-BN, a small portion of the photoresist on the surface of the h-BN is removed, and the catalyst is deposited on an area of the surface of the sheet of h-BN exposed by the removal of photoresist. Then, the remaining photoresist may be removed, leaving a small cluster of atoms of the catalyst on the area of the surface of the sheet of h-BN that was defined by the photoresist.

In some embodiments, a photoresist is used to define a region of the sheet of h-BN that is irradiated with charged particles. For example, the photoresist could be used to define a region of the sheet of h-BN to be irradiated with charged particles to form a defect in the sheet of h-BN, with the photoresist functioning to protect other areas of the sheet of h-BN from irradiation. In some embodiments, a region of the sheet of h-BN is irradiated with charged particles to create a defect in the region. For example, the region may be defined by focusing the charged particles to form a small-diameter beam of the charged particles. As another example, a material having a hole in it may be placed between the sheet of h-BN and the radiation source. The hole in the material may define the region of the h-BN that is irradiated with charged particles.

At block 130, the sheet of h-BN is heated to a temperature above about 500° C. In some embodiments, a temperature above about 500° C. is a temperature of about 510° C., about 525° C., about 550° C., or about 575° C. In some embodiments, the sheet of h-BN is heated to a temperature of about or above about 700° C. In some embodiments, the sheet of h-BN is heated to a temperature of about or above about 900° C. In some embodiments, the sheet of h-BN is heated to a temperature above about 500° C. to about 700° C. In some embodiments, the sheet of h-BN is heated to a temperature above about 500° C. to about 1000° C. The sheet of h-BN may be heated in different environments. For example, in some embodiments, the sheet of h-BN is heated in a vacuum. In some embodiments, the sheet of h-BN is heated in air. In some embodiments, the sheet of h-BN in heated in a specified gas.

At block 140, the defect in the sheet of h-BN is irradiated with charged particles to enlarge the defect to a hexagonal-shaped pore or a parallelogram-shaped pore in the sheet of h-BN. In some embodiments, the pore in the sheet of h-BN does not have a triangular shape. In some embodiments, the sheet of h-BN is irradiated with charged particles when it is at the temperature that it is heated to at block 130. In some embodiments, when the sheet of h-BN is irradiated with charged particles when it is at the temperature that it is heated to at block 130, the sheet of h-BN is cooled to room temperature (e.g., about 21° C. to 23° C.) after block 140.

In some embodiments, the charged particles are electrons, protons, or alpha particles. In some embodiments, the charged particles are electrons, with the electrons having an energy of about 40 kV to 120 kV, or about 80 kV. In some embodiments, the charged particles are reactive ions (i.e., ions that are reactive with the h-BN) or high-energy ions. In some embodiments, the charged particles are oxygen ions, nitrogen ions, argon ions, or gallium ions.

The temperature of the h-BN when it is irradiated with charged particles determines, in part, the shape of the pore that is formed in the sheet of h-BN. For example, at above about 500° C. to about 700° C., the shape of the pore is a parallelogram. Above about 700° C., the shape of the pore is a hexagon. The size of the pore can be controlled by the period of time that the defect in the sheet of h-BN is irradiated. For example, the defect may be irradiated with charged particles for about 15 seconds to 60 seconds, or about 20 seconds to 30 seconds. In some embodiments, a pore has a dimension of about 0.5 nm to 3 nm across the pore, or about 1 nm to 3 nm across the pore. In some embodiments, a hexagonal-shaped pore in the sheet of h-BN has a dimension of about 1 nm to 3 nm across the hexagonal-shaped pore. In some embodiments, a parallelogram-shaped pore in the sheet of h-BN has a dimension of about 1 nm to 3 nm across the parallelogram-shaped pore.

In some embodiments, the atoms along the edge of the pore or the atoms defining the pore are boron and/or nitrogen. In some embodiments, chemical species are not attached to the edges of the pore.

In some embodiments, functional groups are attached to the atoms at the edge of the pore. The functional groups may change the properties of the pore. For example, the functional groups may aid in controlling the motion or storage of chemical species at the pore. In some embodiments, amine groups may be used to link the functional groups to the atoms at the edge of the pore.

Figure 1B:
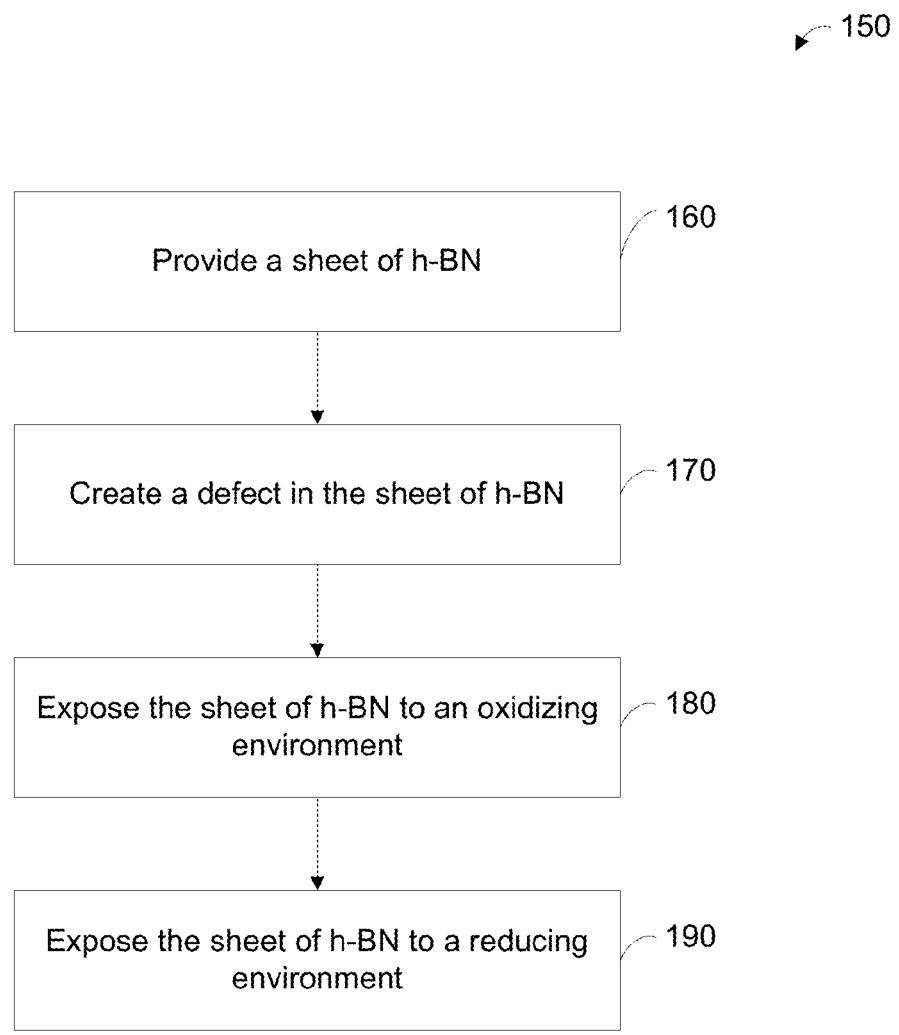
FIG. 1B shows an example of a flow diagram illustrating a method of forming a pore in a sheet of h-BN.

A chemical method also may be used to create a pore in a sheet of h-BN. FIG. 1B shows an example of a flow diagram illustrating such a method of forming a pore in a sheet of h-BN. In some embodiment, the method shown in FIG. 1B is used to form a pore having a specified shape in a sheet of h-BN. Starting at block 160 of the method 150, a sheet of h-BN is provided. The sheet of h-BN may be similar to the sheet of h-BN provided at block 110 as described with respect to FIG. 1A. At block 170, a defect is created in the sheet of h-BN. In some embodiments, the operations at block 170 are similar to the operations at block 120 as described with respect to FIG. 1A. For example, a boron monovacancy can be formed in the sheet of h-BN by charged particle irradiation (e.g., electron irradiation or ion irradiation).

At block 180, the sheet of h-BN is exposed to an oxidizing environment. For example, the sheet of h-BN can be placed in a specific oxidizing environment that preferentially removes dangling nitrogen atoms and enlarges the monovacancy pores while leaving neighboring boron atoms intact. For example, ozone may be used to remove the dangling nitrogen atoms. Performing the method 150 up though block 180 may create a pore in the sheet of h-BN that is large enough for water desalination, for example.

At block 190, the sheet of h-BN is exposed to a reducing environment. Such further processing can be used to remove the boron atoms to enlarge the pore. For example, the sheet of h-BN can be placed in a specific reducing environment that preferentially removes boron atoms (that are now dangling due to removal of nitrogen atoms) and leaves neighboring nitrogen atoms intact. For example, hydrogen at a temperature of about 500° C. to 700° C. may be used to remove the boron atoms.

Blocks 180 and 190 can be repeated until a pore of a specified size is formed in the sheet of h-BN. In some embodiments, block 180 is performed before block 190. In some embodiments, block 190 is performed before block 180. Which of block 180 or block 190 is performed first depends on the atoms defining the vacancy or defect in the sheet of h-BN at block 170. Sequentially exposing the sheet of h-BN to oxidizing environments and reducing environments can be used to controllably form a pore in a sheet of h-BN of a specified size by removing single atoms at a time.

While the above methods specifically refer to h-BN, the methods may be applicable to other two-dimensional materials or multiple layers of other two-dimensional materials. Two-dimensional materials, sometimes referred to as single layer materials, are crystalline materials consisting of a single layer of atoms. For example, the methods may be used to create pores in few-layer or monolayer transition metal dichalcogenides and doped or functionalized graphene (e.g., fluorographene, nitrogen-doped graphene). A two-dimensional material including constituents that have different binding energies and different preferences for how edges are formed may be used as a material in which a pore of a specific geometry may be formed.

Further, while the methods above describe forming a pore in a sheet of h-BN, the methods also can be used to form multiple pores in a sheet of h-BN. For example, for the method 100 shown in FIG. 1, to form multiple pores, multiple defects can be created in the sheet of h-BN at block 120. At block 140, each of the defects can be irradiated with charged particles.

Examples

The following examples are intended to be examples of the embodiments disclosed herein, and are not intended to be limiting.

Below, an investigation of the atomic structure and dynamics of defects in h-BN using 80 kV aberration-corrected transmission electron microscopy (AC-TEM) from room temperature to 1000° C. is presented. Above 700° C., parallelogram- and hexagon-shaped vacancies with pure zigzag edges become prominent. The appearance of 120°-angle-vertices indicates the existence of stable long-range N- and B-terminated zigzag edges. The formation mechanism of the defects in the context of electron irradiation, temperature, and possible etching effects from the surrounding gas environment is discussed. The stability and dynamics of these defects are also examined. Under electron beam radiation, chains of B—N atoms are ejected from the lattice and they can migrate from one to another corner of the open defects at high temperatures. Occasionally topographic defects (pentagon-heptagon or 5|7 pairs) are observed at the defect edges.

Sample Preparation and Initial Characterization h-BN samples were synthesized by a carbothermic reduction reaction between highly oriented pyrolytic graphite (HOPG) flakes, boron oxide powder, and nitrogen gas. In this process, boron and nitrogen replace alternating carbon sites in the HOPG. The converted h-BN flakes were then sonicated in isopropanol for 30 minutes before drop casting on a TEM grid for further microscopy investigation.

Figure 2A:
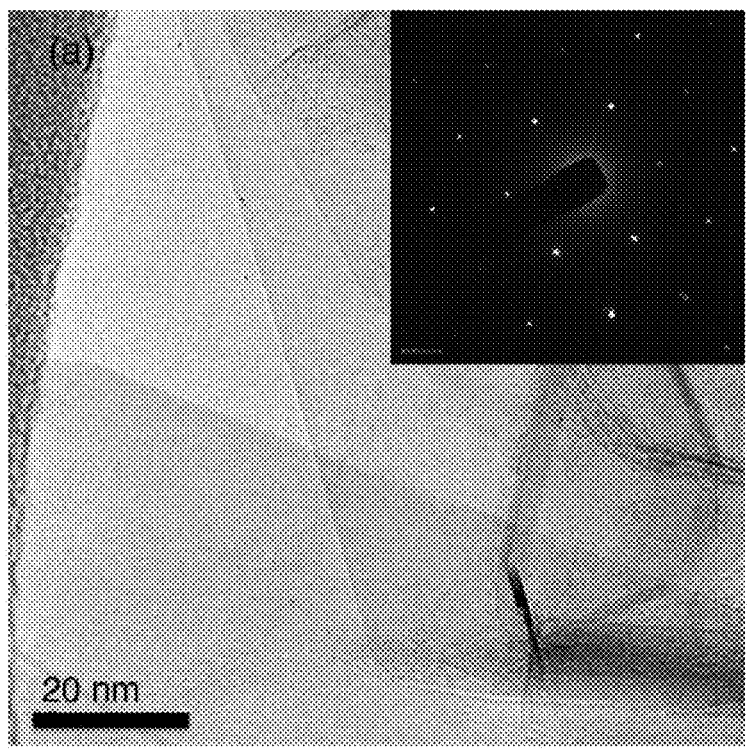
FIGS. 2A-2C show the results of the characterization of as-prepared h-BN flakes.
Figure 2B:
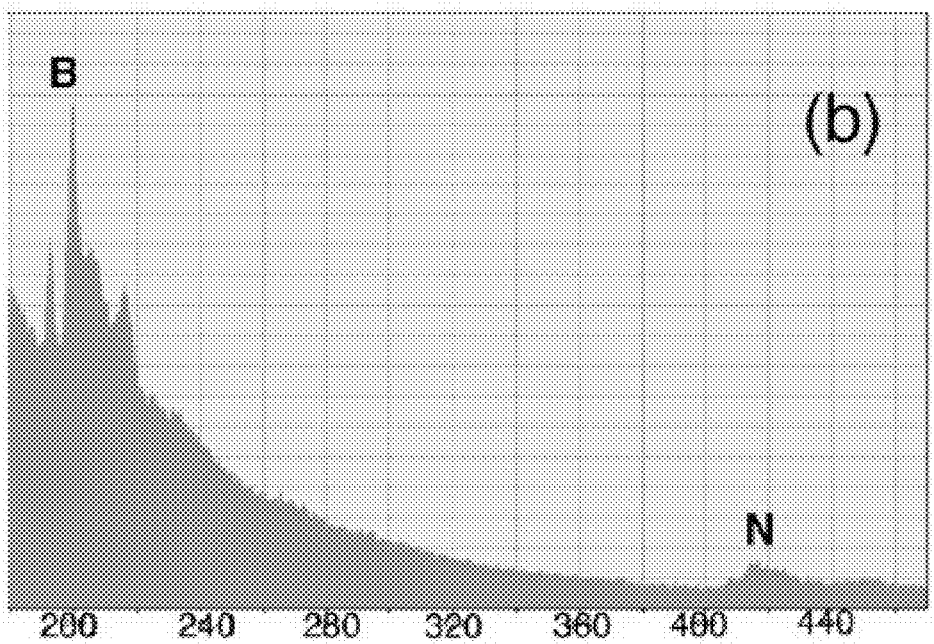
Figure 2C:
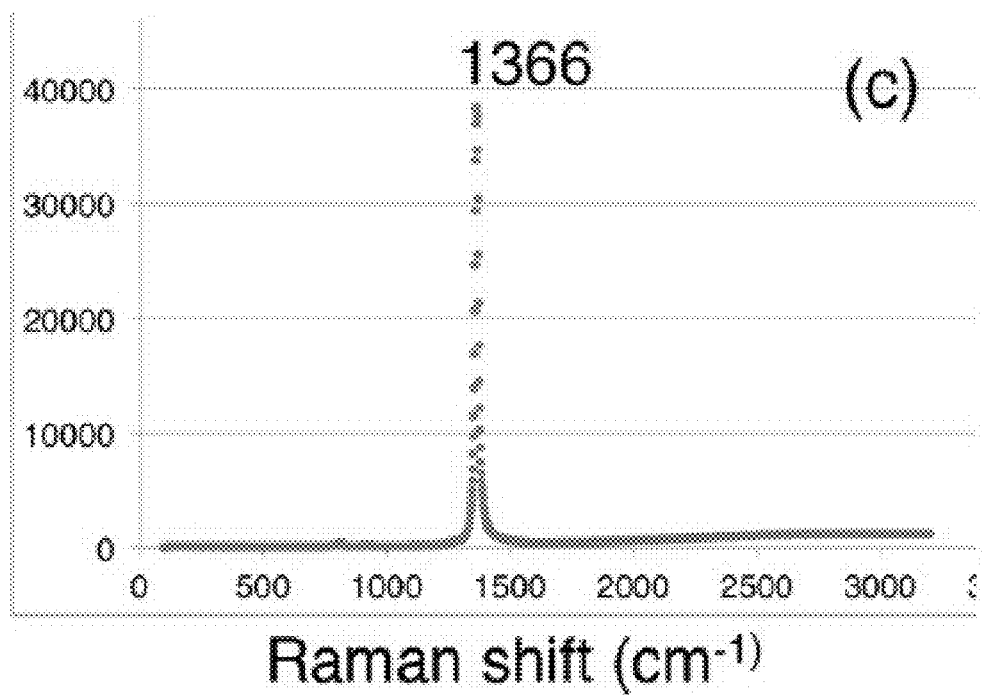

FIGS. 2A-2C show the results of the characterization of as-prepared h-BN flakes. FIG. 2A presents a low-magnification TEM image of the as-synthesized h-BN flakes. The flakes generally consisted of two to five layers and were approximately 3 microns to 5 microns in width. The inset of FIG. 2A shows a corresponding selected area electron diffraction indicating high sample crystallinity. Chemical composition was confirmed by electron energy loss spectroscopy (EELS) and Raman spectroscopy. The EELS spectrum shown in FIG. 2B shows only two edges of K—B and K—N with atomic ratio approximately 1:1, as expected for pure h-BN. The Raman spectrum shown in FIG. 2C shows a prominent peak at 1366 cm$^{-1}$ corresponding to the in-plane vibration mode ($E_{2g}$) of h-BN. There is no peak in either of the EELS or Raman spectra that would indicate the presence of carbon.

Triangular Defects

Figure 3A:
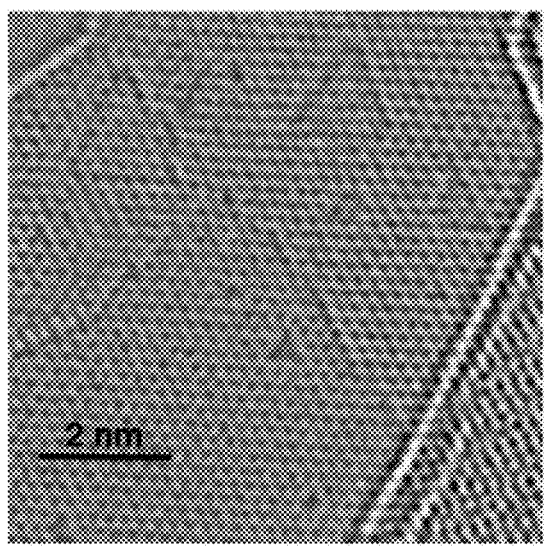
FIGS. 3A and 3B show a representative HRTEM image of triangle defects at 500° C. and a corresponding atomic model.
Figure 3B:
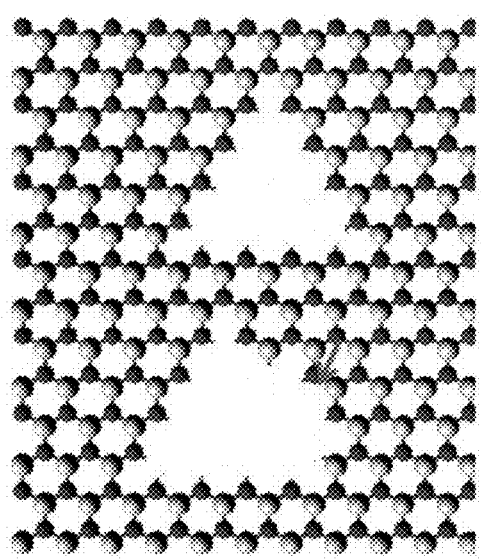

FIG. 3A shows a representative high-resolution transmission electron microscopy (HRTEM) image of triangular defects in h-BN, obtained at 500° C. An atomic model is shown in FIG. 3B (B and N atoms are depicted in gray and black, respectively) for N-terminated zigzag-edge triangles. The image and model shown in FIGS. 3A and 3B also show a triangle with an ejected chain of B—N atoms (indicated by arrows). Triangular defects of this kind are known for h-BN, including for room temperature experiments. The chemical composition of edge-atoms has been confirmed by high resolution EELS and contrast comparison in scanning transmission electron microscopy (STEM) and HRTEM (N appears to have a slightly higher contrast than B).

The defect formation by a knock-on mechanism has been supported widely by both experimental and theoretical studies. As a result of the three-fold symmetry of the h-BN lattice and the asymmetry in displacement threshold of B and N, the defects exhibit triangular shape with exclusively N-terminated zigzag edges. The formation mechanism of triangular defects in h-BN that is observed at 500° C. is likely identical to the mechanism responsible at room temperature. Furthermore, as discussed in more detail below, these observations suggest that triangular defects are enlarged by the ejection of chains of B—N atoms (and not just individual atoms), as has been suggested in the scientific literature.

Hexagonal Defects

At 700° C. the presence of hexagonal defects in addition to the conventional triangles, and at higher temperatures (800° C., 900° C., and 1000° C.) hexagon-shaped defects with distinguishing 120° vertices predominate, are observed. FIGS. 4A-4D show examples of HRTEM images of hexagonal defects at 700° C., 800° C., 900° C., and 1000° C. For each temperature, two images, taken at different times, are shown, which allowed for defect stability and dynamics analysis, as described below.

This atomic-resolution TEM study allowed for direct, clear, and unambiguous identification of the edge structure of hexagonal defects (for example, at 900° C. in FIG. 4C).

FIGS. 5A-5D show additional data recorded at 900° C. FIGS. 5A and 5B show a hexagonal defect, and FIGS. 5C and 5D show a parallelogram. In both cases all edges in the defect are zigzag. Indeed, at all temperatures studied it was found that all hexagonal defect edges adopt a zigzag configuration. The simple h-BN atomic models shown in FIGS. 5B and 5D demonstrate that parallelogram and hexagon-shaped defects (or in general any defect with 120° vertices) with zigzag edges must have both N- and B-terminated atoms.

This key observation apparently contradicts literature wisdom since the presence of a B-terminated zigzag edge has historically been considered metastable and possible only as an intermediate transient construct when the triangle defects grow. Notably, one research group recently observed N monovacancies and B-terminated tetravacancies in h-BN using STEM at 500° C., although no conclusive formation mechanism was provided. It was also found here that extended B-terminated zigzag edges are stable (at least for several seconds under imaging conditions) and ubiquitous (see FIGS. 5A-5D).

Mechanisms for Polygon Defect Formation

The formation mechanism for a polygon defect with both zigzag N- and B-termination edge-atoms in h-BN was examined. Etching effects from the surrounding gas environment, the interaction between the electron beam and the material (both elastic (or knock on) and inelastic interaction), and thermodynamic effects at high temperature were considered.

At low temperature, chemical etchants (residual hydrocarbons and metal atoms) could preferentially attack and remove B atoms, leaving behind exclusively N-terminated defects. High temperature annealing could then remove those etchants from the sample, which indeed eliminates the asymmetry in chemical reactivity of B and N. B and N would then be ejected with similar probability, resulting in both N- and B-terminated defect-edges. It is worth mentioning, however, that even at high temperatures the etching effect from the surrounding gas environment should not be excluded and it makes the problem more complicated. Although the TEM column has very high vacuum, there might still be present trace amounts of gases and water vapor. Under electron beam radiation, free radicals are created from the radiolysis of those gas molecules. They can be considered as highly reactive etchants, contributing to defect formation and instability in h-BN. Experiments performed under a controlled gas environment (e.g., using environmental TEM) may provide useful information about the role of gas environment to the formation and stability of defects in h-BN and graphene.

The effect of high temperatures and electron beam radiation was also considered. Previous models considered a static lattice, which explains the defect formation by elastic damage at room temperature and in the range of 80 kV to 120 kV. At high temperature, the combination of lattice vibration, elastic interaction, and even inelastic damage must be taken into account. In addition, many external factors, such as strain, can dramatically change the band structure of boron nitride, leading to changes in interaction with the beam. During heating, strain can be caused by the thermal contraction or expansion of the lattice. Boron nitride has a negative coefficient of thermal expansion, so as it is heated it will shrink. However, most substrates, including those used to suspend h-BN for TEM studies, have a positive coefficient of thermal expansion and thus will expand when heated, leading to substrate-film strain. All of the aforementioned factors may contribute to a convergence of knock-on ejection threshold for B and N at high temperature. With the probability of lattice ejection equal between B and N, the three-fold symmetry of h-BN becomes a six-fold symmetry, and the material will adopt hexagon-shaped vacancies, as observed.

Another possible explanation for the change in defect shapes at higher temperatures is due to a trade-off between the entropically and enthalpically preferred structures. This stability is explained by the Gibb's Free Energy equation, $$\Delta G = \Delta H - T\Delta S$$

where $\Delta G$ is the Gibb's Free Energy, $\Delta H$ is the enthalpy, T is temperature, and $\Delta S$ is the entropy. Because defects increase the disorder of a material, they are naturally an entropically favored structure in comparison to a perfect crystal. However, the specific structure of the preferred defects has been experimentally observed to change with temperature. As the temperature of the system increases, as in the experiments above, the system becomes more entropically dominated. It is proposed that at low temperatures, 60° angles are the enthalpically preferred defect configuration. At high temperatures above 500° C., the more entropically favored 120° angles are allowed.

Stability and Dynamics of Polygon Defects

The stability and dynamics of hexagonal defects was investigated first. FIGS. 6A-6L show selected 900° C. HRTEM images and corresponding atomic models, which show the structural evolution of a polygon vacancy over time. The dotted circles indicate an atom or chain of atoms, which disappear in the following time frame, or newly added atoms. It is noted that for the images in FIGS. 5A-5D and 6A-6L, B and N are on an equal footing and can be generally interchanged without losing the generic nature of the observation and conclusion. In other words, the black and gray spheres can be respectively B and N, or vice versa. The observations suggest that parallelogram and hexagonal vacancies (or in general any zigzag edge with 120° vertices) will always have both black and gray-terminated (i.e., B and N-terminated) zigzag edges.

Figures 6A, 6B, 6C, 6D:
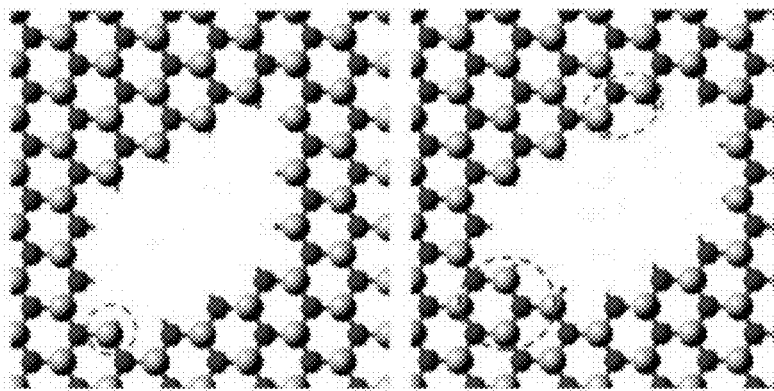
FIGS. 6A-6L show HRTEM images and the corresponding atomic models illustrating the stability and dynamics of a polygon defect at 900° C. The dotted circles indicate atom or chain of atoms, which will be removed in the next time frame, or newly added atom(s). Scale bars are 2 nanometers.
Figures 6E, 6F, 6G, 6H:
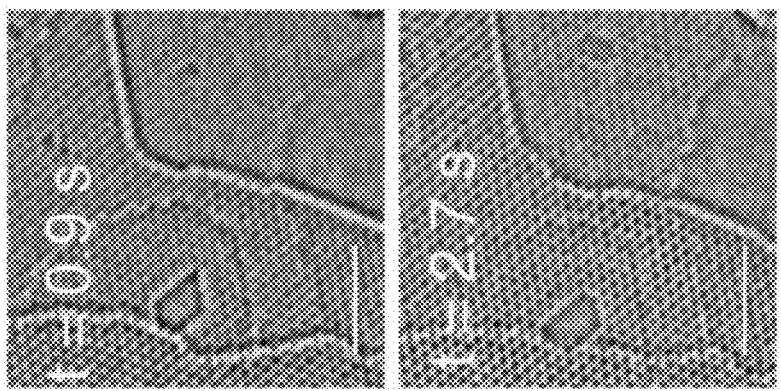
Figure 6L:
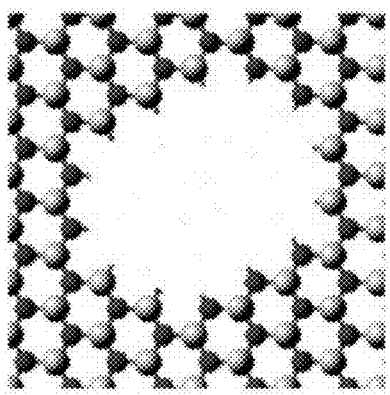
Figure 6K:
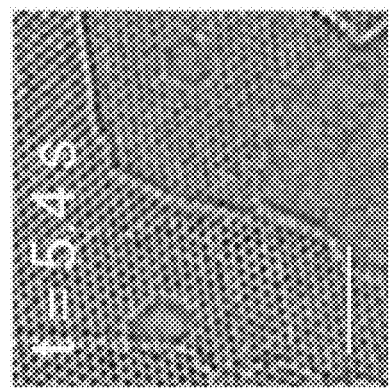
Figure 6J:
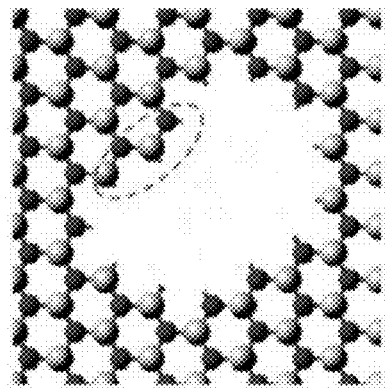
Figure 6I:
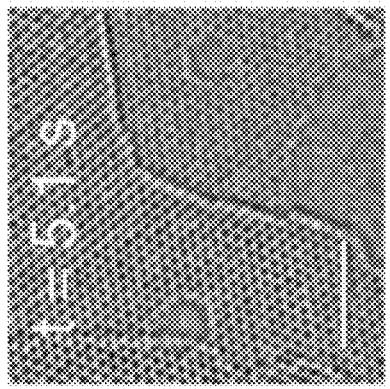
Figures 7A, 7B, 7C:
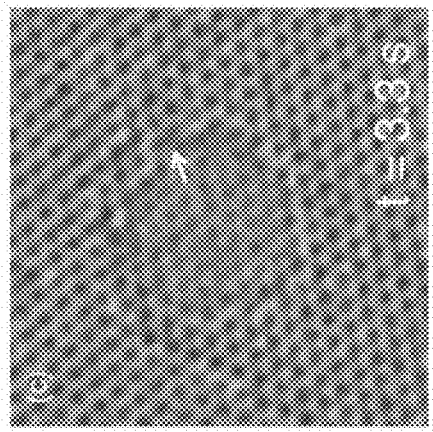
FIGS. 7A-7F show HRTEM images of a hexagon defect at 900° C.
Figures 7D, 7E, 7F:
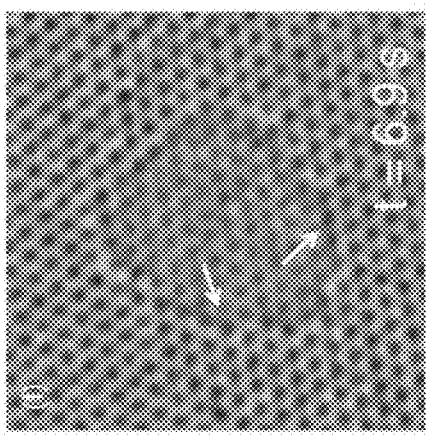

The polygon defect shown in FIGS. 6A and 6B is stable for 0.6 seconds, before the first atoms are knocked-out (as marked at t=0.3 seconds and 0.9 seconds) to adopt a parallelogram-shaped defect. The parallelogram pore is stable for 0.9 seconds and after that (at t=2.7 seconds) a chain of B—N atoms is removed (dotted circle) while a cluster of 4 B—N atoms is added (dotted circle). Since this structural reconstruction happens at high temperature (900° C.), the healing of the defect (at the top corner as marked by a dotted circle at t=2.7 seconds in FIG. 6H) can be realized by the migration of the removed atoms from the same defect (marked by the dotted circle at t=1.8 seconds in FIG. 6F) or ejected atoms from the nearby step edges. The trapezoid defect is stable for 2.4 seconds (from t=2.7 seconds to t=5.1 seconds) before chains of B—N atoms are removed at t=5.1 seconds and t=5.4 seconds to adopt a hexagonal shape. It is interesting to note that in the nearby monolayer area there is another defect, and over time this defect also evolves into a hexagon (see the frame at t=5.4 seconds) with the same orientation.

FIGS. 7A-7F show another example of possible ejections of groups of B—N atoms during the formation of hexagon defects. This again emphasizes the symmetry of the ejection probability of the two elements under the imaging condition (i.e., 900° C.). The defects grow in a manner that retains the overall 120° angles at defect-vertices by ejecting out a single row or rows of atoms at a time.

Topological Defects at the Inner Edges

Figure 8A:
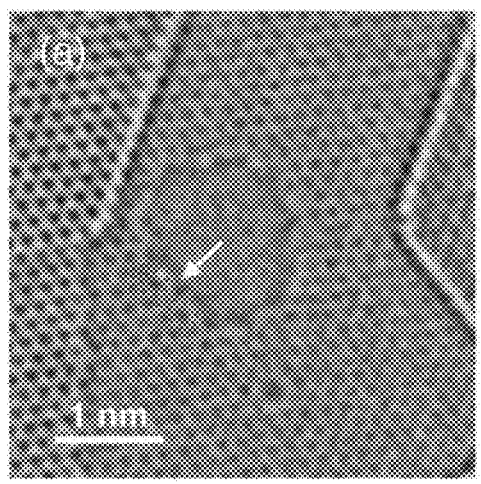
FIGS. 8A and 8B show HRTEM images of topographic defects (pentagon-heptagon (5|7) pairs) at the defect edge in h-BN (at 900° C.). Dots illustrate atom positions and arrows indicate topographic defects.
Figure 8B:
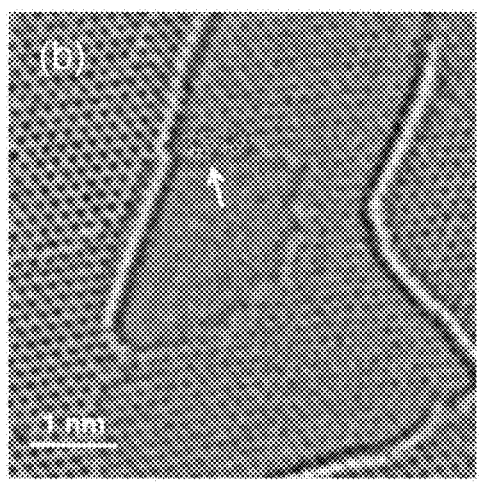

Edge reconstruction of h-BN at high temperature and under electron beam irradiation was also studied. In the case of graphene, edge reconstruction from armchair to zigzag, and from zigzag to 5|7-zigzag, edges are readily seen under electron beam irradiation. In h-BN, due to its elemental heterogeneity, 5|7 topographic defects are energetically unfavorable since they involve homonuclear bonds between B—B and N—N. Previous studies show the occasional presence of such defects during imaging. There is a special case where these 5|7 defects are particularly stable, and that is at the grain boundaries of h-BN. Here the lattice strain at the grain boundaries compensate their high formation energy. However, there is no study reporting the presence of these topological defects at the edge of h-BN. FIGS. 8A and 8B clearly show the presence of 5|7 pairs. Due to the unfavorable nature of this defect and the fast dynamics occurring at the edges, these defects usually exist in one frame and then either relax back to 6-member rings or are ejected. Further studies with shorter exposure time and a faster scanning camera might capture the dynamics of these defects and shed light on edge reconstruction in h-BN.

Applications of Few-Layer and Monolayer Hexagonal Boron Nitride

Few-layer and monolayer sheets having a pore or pores formed therein are an emerging candidate for DNA/RNA sequencing and molecular analysis. A pore in a thin sheet can be used to separate two reservoirs of an analyte-containing (e.g., molecules, such as DNA or long chain polymers) ionic solution. An applied voltage between the two reservoirs can be used to drive an ionic current through the pore. This ionic current can then push analyte molecules through the pore. The translocation of these molecules through the pore causes a blockade of ionic current between the reservoirs. The current blockade is characteristic of a given molecule or part of a molecule. For example, in the case of single strand DNA, ionic current can push DNA through a pore, where each base pair then causes a different current blockade. This current blockade can be measured and the DNA sequence can be determined.

While biological pores have been used to sequence DNA with error of 4% to 25%, previous attempts to sequence DNA with solid state pores have not yet achieved single base pair resolution. Achieving this resolution with a solid state pore would represent a breakthrough in pore sequencing, as solid state pores are typically more scalable than their biological counterparts.

Due to its atomic scale thickness, pores in graphene are being studied for DNA sequencing. However, processes for forming a pore in graphene described in the literature do not produce a pore of repeatable size or geometry. This lack of pores of repeatable size or geometry is one factor limiting the performance of the graphene pores. Additionally, due to the organic nature of graphene, the edges of the pore may attract various functional groups, which may further impede measurement. That is, a pore in graphene may not have pure carbon edges. Further, graphene is electrically conductive, which may also limit the performance of graphene pores in some applications.

Figure 9:
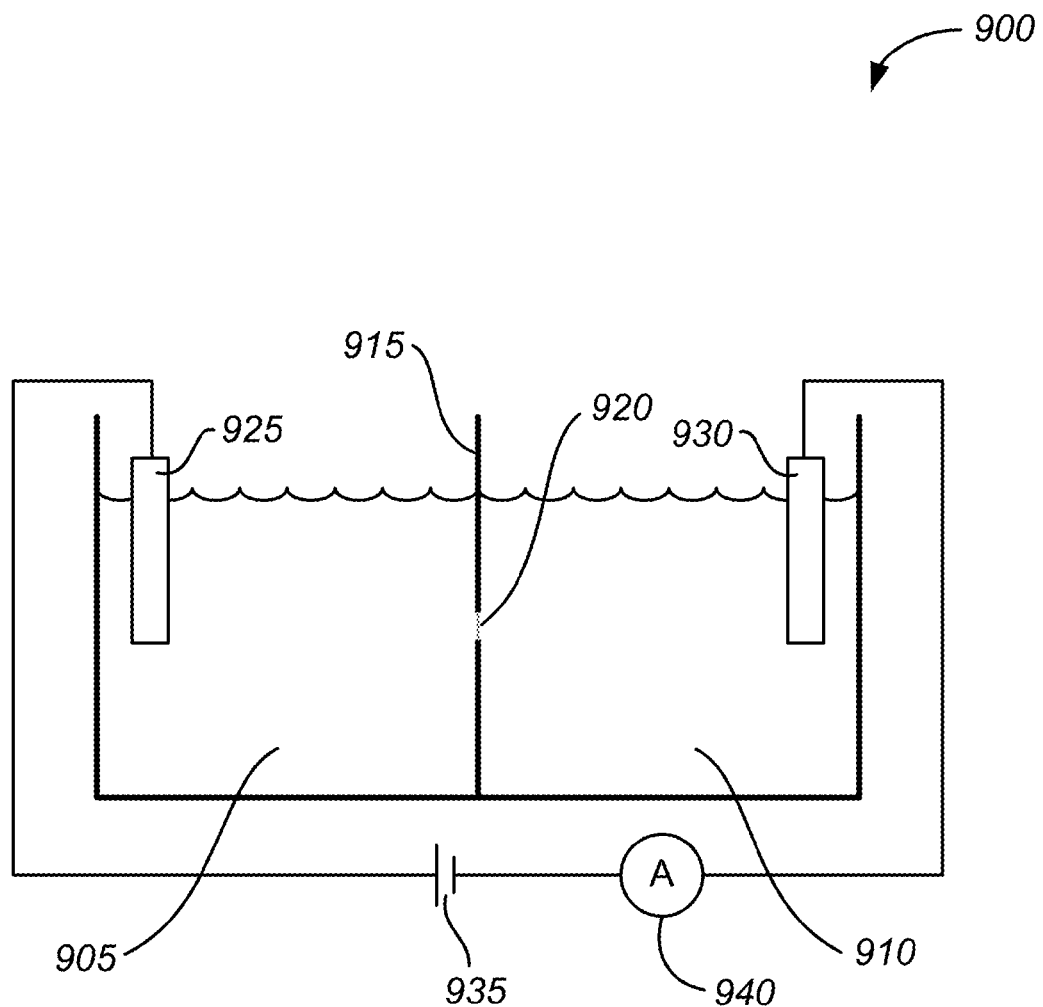
FIG. 9 shows an example of a cross-sectional schematic illustration of an apparatus for sequencing DNA.

FIG. 9 shows an example of a cross-sectional schematic illustration of an apparatus for sequencing DNA. The apparatus 900 shown in FIG. 9 includes a first chamber 905 and a second chamber 910 separated by separator 915 having a sheet of h-BN 920 disposed therein. The sheet of h-BN 920 is held by or is mounted in the separator 915, with the separator 915 and the sheet of h-BN 920 separating the first chamber 905 and the second chamber 910. In some embodiments, the sheet of h-BN 920 may be small, having dimensions of less than 1 centimeter (cm) by 1 cm.

The first chamber 905 and the second chamber 910 are configured so that a liquid may be disposed in the first and the second chambers. A first electrode 925 is positioned in the first chamber 905 so that it is in contact with the liquid. A second electrode 930 is positioned in the second chamber 910 so that it is in contact with the liquid. In some embodiments, the apparatus 900 includes a power source (e.g., a DC power source) 935 and an ammeter 940.

A pore (not shown) in the sheet of h-BN 920 allows the first chamber 905 and the second chamber 910 to be in fluid communication with one another. In some embodiments, the sheet of h-BN 920 is a monolayer of h-BN. In some embodiments, the sheet of h-BN 920 comprises multiple layers of h-BN. In some embodiments, the pore has a shape selected from a group consisting of a triangular shape, a hexagonal shape, and a parallelogram shape. In some embodiments, the pore in the sheet of h-BN has a dimension of about 0.5 nm to 3 nm across the pore. In some embodiments, a triangular pore is about 1 nm to 3 nm across the triangle, or about 1 nm to 2 nm across the triangle. In some embodiments, the pore is defined by atoms selected from a group consisting of nitrogen atoms, boron atoms, and combinations thereof. In some embodiments, functional groups are attached to atoms defining the pore.

The sheet of h-BN is not electrically conductive (i.e., it is electrically insulating). This may improve the performance of the apparatus 900 in some instances. In some embodiments, instead of h-BN, a different few-layer or monolayer sheet of a two dimensional material described herein having a pore defined therein separates the first chamber 905 and the second chamber 910.

In some embodiments, the liquid comprises water. In some embodiments, the water includes ions dissolved therein. For example, in some embodiments, a salt is dissolved in the water. In some embodiments, the salt comprises potassium chloride, sodium chloride, calcium chloride, or magnesium chloride. In some embodiments, the liquid comprises a biological buffer solution.

Figure 10:
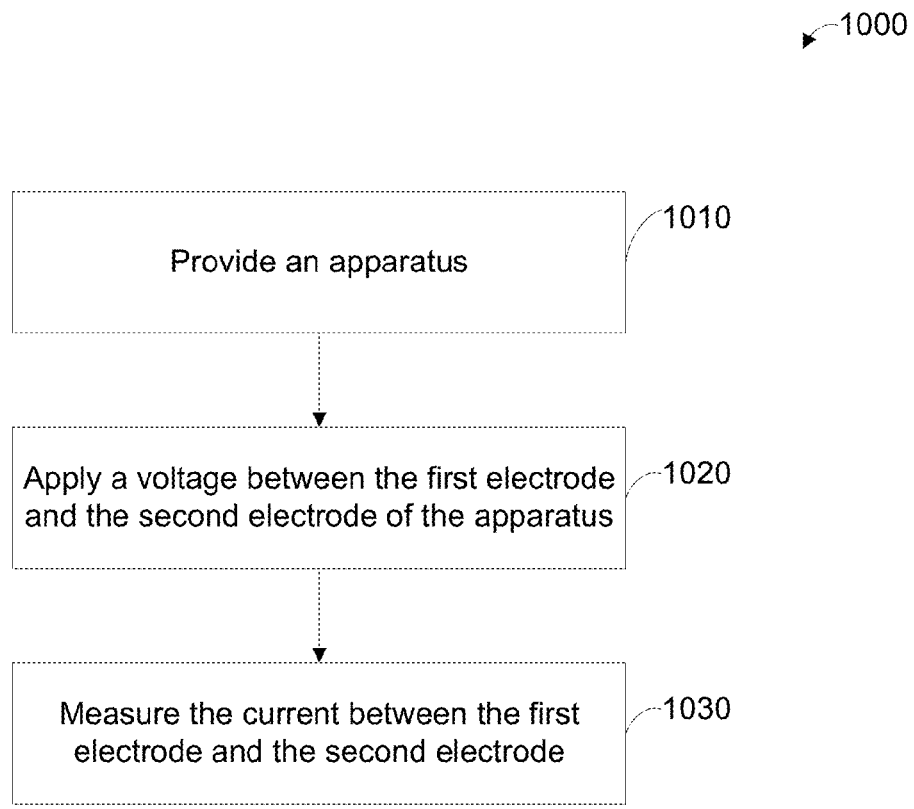
FIG. 10 shows an example of a flow diagram illustrating a method of sequencing DNA.

FIG. 10 shows an example of a flow diagram illustrating a method of sequencing DNA. At block 1010 of the method 1000 shown in FIG. 10, an apparatus is provided. In some embodiments, an apparatus similar to the apparatus 900 described with respect to FIG. 9 is provided.

With a liquid disposed in the first chamber and the second chamber of the apparatus, a voltage is applied to the first electrode and the second electrode of the apparatus at block 1020. In some embodiments, the voltage is about 1 mV to 2 V, or about 500 mV. For example, when a negative bias is applied to the first electrode and a positive bias is applied to the second electrode, negatively charged ions will flow from the first chamber to the second chamber.

At block 1030, a current between the first electrode and the second electrode is measured. When a stand of DNA in the first chamber travels to the second chamber through the pore in the sheet of h-BN, the order of the nucleotides within the strand DNA can be identified by the variations in the current. For example, the ionic current from the first chamber to the second chamber may push the strand of DNA though the pore. When the DNA is in the pore, the ionic current between the first electrode and the second electrode will be blocked. The variations in the current when the stand of DNA is traveling though the pore can be used to sequence the strand of DNA.

Sheets of h-BN including pores integrated in devices that separate two reservoirs of a gas or a liquid can also be used in other applications. For example, for gas/liquid separation, a sheet of h-BN with multiple pores sized such that a single molecule or hydrated atom species is able to pass through the sheet can be used to separate two reservoirs. The molecules or atoms can then be separated from the initial solution or vapor. This technology potentially will be useful for batteries and energy storage, air filtration, and alcohol manufacture.

As another example, as a subset of the gas/liquid separation application, sheets of h-BN including pores may be used for low-energy water desalination. In this case, the pores are large enough to allow water to pass through, but small enough to block hydrated ions, such as, for example, potassium, chlorine, and sodium.

CONCLUSION

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. A method comprising:
   (a) providing a sheet of hexagonal boron nitride (h-BN);
   (b) creating a defect in the sheet of h-BN by depositing a catalyst on the sheet of h-BN and heating the catalyst;
   (c) heating the sheet of h-BN to a temperature above about 500° C.; and
   (d) irradiating the defect in the sheet of h-BN with charged particles to enlarge the defect to a hexagonal-shaped pore or a parallelogram-shaped pore in the sheet of h-BN.

2. The method of claim 1, further comprising:
   fabricating the sheet of h-BN.

3. The method of claim 1, wherein the charged particles comprise particles selected from a group consisting of electrons, protons, and alpha particles.

4. The method of claim 1, wherein the charged particles comprise electrons, and wherein the electrons have energies of about 40 kV to 120 kV.

5. The method of claim 1, wherein the hexagonal-shaped pore or the parallelogram-shaped pore in the sheet h-BN has a dimension of about 1 nanometer to 3 nanometers across the hexagonal-shaped pore or the parallelogram-shaped pore.

6. The method of claim 1, wherein the catalyst comprises a transition metal.

7. The method of claim 1, wherein the catalyst comprises a metal selected from a group consisting of iron, cobalt, and nickel.

8. The method of claim 1, wherein the sheet of h-BN is heated to a temperature of about 700° C. in operation (c).

9. The material of claim 1, wherein the sheet of h-BN comprises a monolayer of h-BN.

10. The method of claim 1, wherein the catalyst is heated using a laser in operation (b).

11. The method of claim 1, wherein the catalyst reacts with the sheet of h-BN to form the defect in operation (b).

12. The method of claim 1, wherein the catalyst comprises a single atom of the catalyst.

13. The method of claim 1, wherein the catalyst comprises a cluster of atoms of the catalyst.

14. The method of claim 1, wherein the catalyst comprises a nanoparticle.

15. The method of claim 1, wherein the catalyst has dimensions of about 1 nanometer or less than about 1 nanometer.

16. The method of claim 1, wherein photolithography is used to define an area of the sheet of h-BN on which the catalyst is deposited in operation (b).

17. The method of claim 1, wherein the charged particles comprise oxygen ions, nitrogen ions, argon ions, or gallium ions.

18. The method of claim 1, wherein defect in the sheet of h-BN is irradiated with charged particles for about 15 seconds to 60 seconds in operation (d).

19. The method of claim 1, further comprising:
   functionalizing the hexagonal-shaped pore or the parallelogram-shaped pore in the sheet of h-BN.

20. The method of claim 1, wherein the catalyst is deposited on the sheet of h-BN in operation (b) by evaporation, chemical vapor deposition, atomic layer deposition, or sputtering.

\* \* \* \* \*